(12) United States Patent
Yoon et al.

(10) Patent No.: US 10,500,022 B2
(45) Date of Patent: Dec. 10, 2019

(54) MULTIFUNCTIONAL ORAL PROSTHETIC SYSTEM

(71) Applicants: University of Florida Research Foundation, Inc., Gainesville, FL (US); The Research Foundation of State University of New York, Amherst, NY (US)

(72) Inventors: Yong-Kyu Yoon, Gainesville, FL (US); Gloria J. Kim, Gainesville, GA (US); Xiaoyu Cheng, Gainesville, FL (US); Marc Campillo-Funollet, West Seneca, NY (US); Carlos A. Munoz, Williamsville, NY (US)

(73) Assignees: UNIVERSITY OF FLORIDA RESEARCH FOUNDATION, INC., Gainesville, FL (US); THE RESEARCH FOUNDATION OF STATE UNIVERSITY OF BAIRD RESEARCH PARK, Amherst, NY (US)

( * ) Notice: Subject to any disclaimer, the term of this patent is extended or adjusted under 35 U.S.C. 154(b) by 171 days.

(21) Appl. No.: 14/347,951

(22) PCT Filed: Sep. 27, 2012

(86) PCT No.: PCT/US2012/057526
§ 371 (c)(1),
(2) Date: Mar. 27, 2014

(87) PCT Pub. No.: WO2013/049327
PCT Pub. Date: Apr. 4, 2013

(65) Prior Publication Data
US 2014/0248574 A1    Sep. 4, 2014

Related U.S. Application Data

(60) Provisional application No. 61/540,183, filed on Sep. 28, 2011.

(51) Int. Cl.
*A61C 13/00* (2006.01)
*A61C 13/01* (2006.01)
(Continued)

(52) U.S. Cl.
CPC ............ *A61C 13/0024* (2013.01); *A61C 7/14* (2013.01); *A61C 13/01* (2013.01); *A61C 13/08* (2013.01); *A61C 19/04* (2013.01); *A61C 19/063* (2013.01)

(58) Field of Classification Search
CPC ... A61C 19/04; A61C 19/063; A61C 13/0024; A61C 13/01; A61C 19/05; A61C 19/045;
(Continued)

(56) References Cited

U.S. PATENT DOCUMENTS

| 5,078,153 A | 1/1992 | Nordlander et al. |
| 6,089,864 A | 7/2000 | Buckner et al. |

(Continued)

FOREIGN PATENT DOCUMENTS

| EP | 1245197 A2 | 10/2002 |
| WO | 2005115225 A2 | 12/2005 |

(Continued)

OTHER PUBLICATIONS

Igarashi, Yoshimasa. "Analysis of the Denture Dynamics in RPD's". 1989. Journal of Japanese Prosthdont Society, 33:369-375.*
(Continued)

*Primary Examiner* — Edward Moran
(74) *Attorney, Agent, or Firm* — Thomas | Horstemeyer, LLP (57) ABSTRACT

Various methods and systems are provided for multifunctional denture systems. In one example, among others, a multifunctional oral prosthetic system includes an oral prosthetic device that may be located in an oral cavity. The oral prosthetic device includes a plurality of sensors and an
(Continued)

internal module in communication with the plurality of sensors. The internal module is configured to provide sensor data corresponding to at least one of the plurality of sensors to an external processing unit when located in an oral cavity.

21 Claims, 8 Drawing Sheets

(51) Int. Cl.
*A61C 19/04* (2006.01)
*A61C 7/14* (2006.01)
*A61C 13/08* (2006.01)
*A61C 19/06* (2006.01)

(58) Field of Classification Search
CPC .......... A61C 7/07; A61C 7/14; A61B 5/1072; A61B 5/1075–1076; A61B 5/682; A61B 5/4542–4557; A61B 5/6885–6886; A61B 2562/0257
USPC .................. 433/6, 27, 202.1, 215, 218, 229; 600/590, 587
See application file for complete search history.

(56) References Cited

U.S. PATENT DOCUMENTS

| | | | |
|---|---|---|---|
| 6,122,961 A * | 9/2000 | Geen | G01C 19/5719 73/504.12 |
| 6,941,952 B1 | 9/2005 | Rush, III | |
| 2006/0166157 A1* | 7/2006 | Rahman | A61B 5/4833 433/6 |
| 2006/0210951 A1 | 9/2006 | Levanoni | |
| 2006/0271199 A1 | 11/2006 | Johnson | |
| 2007/0106138 A1* | 5/2007 | Beiski et al. | 600/349 |
| 2009/0220563 A1* | 9/2009 | Shachar | 424/423 |
| 2009/0237236 A1 | 9/2009 | Maassarani | |
| 2011/0008744 A1* | 1/2011 | Teggatz | A61C 19/063 433/1 |
| 2011/0066066 A1 | 3/2011 | Van Kemenade et al. | |
| 2011/0184319 A1 | 7/2011 | Mack et al. | |
| 2011/0184663 A1 | 7/2011 | Mack et al. | |
| 2012/0172679 A1 | 7/2012 | Logan et al. | |
| 2013/0066236 A1 | 3/2013 | Herman et al. | |
| 2013/0211270 A1 | 8/2013 | St Laurent et al. | |
| 2014/0187875 A1 | 7/2014 | Paris et al. | |
| 2014/0188010 A1 | 7/2014 | Paris et al. | |
| 2015/0305671 A1 | 10/2015 | Yoon et al. | |

FOREIGN PATENT DOCUMENTS

| WO | 2008/061328 | 5/2008 |
|---|---|---|
| WO | 2016/183442 | 11/2016 |

OTHER PUBLICATIONS

Igarashi; "Analysis of the denture dynamics in RPD's"; J Jpn Prosthodont Soc, 33 (2): 1989, pp. 369-375.*
Translation of "Analysis of the denture dynamics in RPD's".*
No Author, mHealth New Horizons for Health Through Mobile Technologies, Global Observatory for eHealth Series, vol. 3, World Health Organization, Jun. 20, 2011.
Alvarez, A.; Barrientos, A.; Lantada, A.; Morgado, P.; Cepeda, P.; Herranz, R.; "Diagnosis of Bruxism Based on Polymeric Piezoelectric Sensors and Remote Communication", [Online]. Available: http:ffwww.disam.upm.Desf.
Andres Diaz Lantada, Handbook of Active Materials for Medical Devices: Advances and Applications, Pan Stanford Publishing, Singapore, 2012, pp. 199-207.
Gonzalez, C.; Lantada, A., "A wearable passive force sensor powered by an active interrogator intended for intra-splint use for the detection and recording of bruxism," Pervasive Computing Technologies for Healthcare, 2009. D PervasiveHealth 2009. 3rd International Conference on , pp. 1-4, Apr. 1-3, 2009.
H. Takeuchi, et al. "A piezoelectric film based intra-splint detection method for bruxism"?, The Journal of Prosthetic Dentistry, vol. 86, issue 2, pp. 195-202, Aug. 2001.
International Search Report for PCT/US2012/057526 dated Apr. 22, 2013.
J. Clauss, M. Sattler, W.O. Seeher and B. Wolf, "In-vivo monitoring of bruxism with an intelligent tooth splint—Reliability and validity"?, IFMBE Proceedings, vol. 25, No. 11, pp. 108-111, Sep. 2009.
Jules Kieser, et al., "Measuring Intraoral Pressure: Adaptation of a Dental Appliance Allows Measurement During Function"?, Dysphagia, vol. 23, No. 3, pp. 237-243, 2008.
Jung Ho Kim; McAuliffe, P.; O'Connel, B.; Diamond, D.; King Tong Lau; , "Development of Bite Guard for Wireless Monitoring of Bruxism Using Pressure-Sensitive Polymer," Body Sensor Networks (BSN), 2010 International D Conference on, pp. 109-116, Jun. 7-9, 2010.
Jungho Kim, et ai"Development of wireless bruxism monitoring device based on pressure sensitive polymer composite", Sensors and Actuators A, vol. 163, pp. 486-492, 2010.
K. Ahlberg, et al., "Bruxism and sleep efficiency measured at home with wireless devices"?, Journal of Oral Rehabilitation, vol. 35, pp. 567-571, 2008.
M.C. Raadsheer, et al., Contribution of Jaw Muscle Size and Craniofacial Morphology to Human Bite Force Magnitude, Journal of Dental Research, vol. 78, No. 1, pp. 31-42, Jan. 1999.
Mart A.; Barrientos, A .. ; Lafont, P.; Colorado, J.; Castedo, P.L.; Gonz, R.; , "Polymeric piezoelectric sensors and remote communication for detection of bruxism," Industrial Technology {1 CIT), 2010 IEEE International Conference on , D pp. 268-273, Mar. 14-17, 2010.
Takahashi S, Ono T, Ishiwata Y, and Kuroda T., "Effect of changes in the breathing mode and body position on tongue pressure with respiratory related oscillations"?, Am J. Orthod Dentofacial Orthop., vol. 115, No. 3, pp. 239-246, Mar. 1999.

* cited by examiner

FIG. 1

Presence of Human body (a)

MULTIFUNCTIONAL ORAL PROSTHETIC SYSTEM

CROSS REFERENCE TO RELATED APPLICATIONS

This application is the 35 U.S.C. § 371 national stage of PCT Application No. PCT/US2012/057526, entitled "Multifunctional Oral Prosthetic System" and filed Sep. 27, 2012, which is hereby incorporated by reference in its entirety, and which claims priority to, and the benefit of, U.S. Provisional Application No. 61/540,183, filed Sep. 28, 2011, which is hereby incorporated by reference in its entirety.

BACKGROUND

Dental disease can result in damage to the gum tissue and ultimately in the loss of teeth. Often, prosthetic devices such as dentures are used to replace the missing teeth. The prosthetic device is supported by surrounding soft and hard tissues of the oral cavity. One of the most common problems with dentures is keeping them in place. Denture movement not only leads to discomfort, but may result in additional damage to the oral tissues. In general, dentists rely on tactile sensing to ascertain fit during in-office visits. However, such an invasive examination is hardly an accurate reflection of the environment the dentures are subjected to during the normal day-to-day routine of the wearer.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Disclosed herein are various embodiments of systems and methods related to multifunctional denture systems. Reference will now be made in detail to the description of the embodiments as illustrated in the drawings, wherein like reference numbers indicate like parts throughout the several views.

In situ monitoring of changes in the conditions such as distance, pressure, and movement allows for evaluation of an individual's oral condition over time. In addition, saliva can provide information not only on the state of the oral cavity, but also on the systemic health of the individual. Other in situ monitoring may also be used to evaluate and identify speech patterns and/or impediments. Advancement of microelectronic and sensor technologies can provide implantable or minimally invasive biomedical devices for oral applications. Additionally, developments in nanotechnology and microelectromechanical system (MEMS) technology have miniaturized sensors with increased sensitivity and selectivity, providing the ability to monitor a wide range of conditions. This disclosure presents a multifunctional denture system that includes an integrated system capable of multiplexed detection and in situ monitoring for diagnostics and prognostics without invasive examination.

Figure 1:
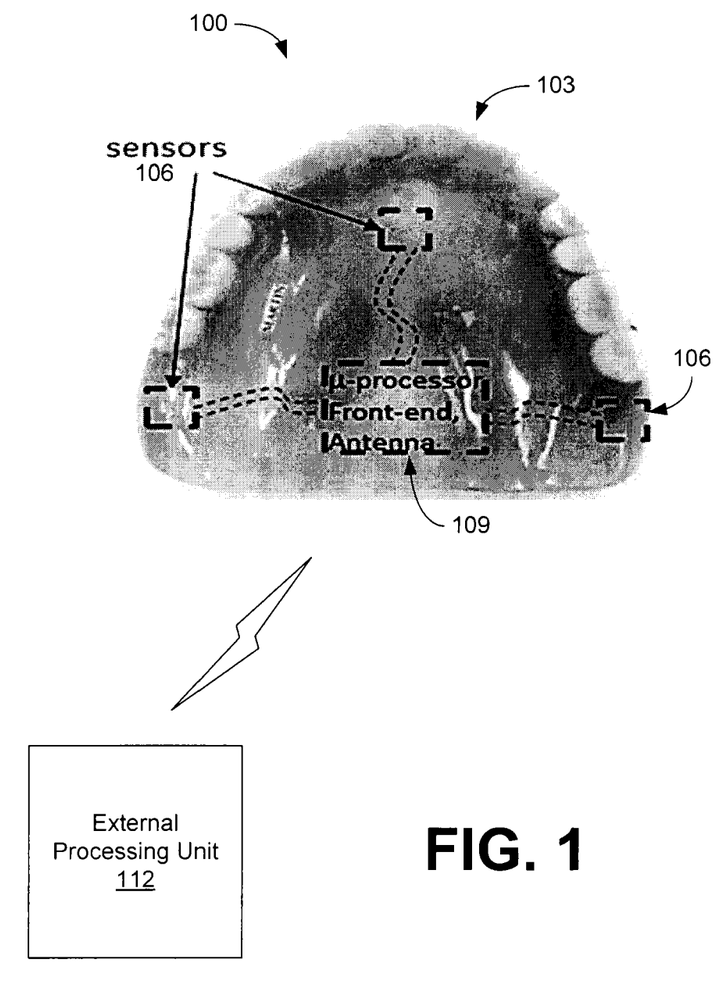
FIG. 1 is an example of a multifunctional denture system in accordance with various embodiments of the present disclosure.

Referring to FIG. 1, shown is an example of a multifunctional denture system 100. The multifunctional denture system 100 includes a denture 103 (full or partial) that is a prosthetic device constructed to replace missing teeth and which is supported by surrounding soft and hard tissues of the oral cavity. The denture 103 (full or partial) includes one or more sensor(s) 106 such as, e.g., displacement sensors to measure the distance (or gap) between the denture and oral tissue; stress/strain sensors to gauge denture dislocation, pressure, and movement; temperature sensors to survey the oral cavity environment for assessment of oral and physiologic system health; and/or various chemical sensors and biomedical sensors to monitor, e.g., pH, glucose, or enzymes and for diagnostics and prognosis of clinical problems such as, e.g., oral diseases, HIV, cancer, and diabetes. Nanotechnology and microelectromechanical system (MEMS) technology have driven the development of sensors 106 with increased sensitivity and selectivity. The sensors 106 are communicatively coupled to an internal module 109 for data and signal processing. The internal module 109 is configured to gather information from the sensors 106 and transmit the gathered data to an external processing unit 112.

The internal module 109 includes, e.g., a microprocessor to process data from the sensors 106. The internal module 109 may include a sensor front end and/or an analog-to-digital converter (ADC) for obtaining data from the sensors 106 and providing the data to the microcontroller in the appropriate format. The internal module 109 may also include a transceiver and antenna for wireless data transmission (e.g., a radiofrequency, microwave, or other appropriate transmission) of the data to the external processing unit 112 for further processing and evaluation. The external processing unit 112 may be a computing device configured to render for display the data obtained from the internal module 109. In the example of FIG. 1, the sensors 106 and the internal module 109 of the multifunctional denture system 100 are embedded in a full denture 103. In other embodiments, sensors 106 may be affixed to a surface of the denture 103, orthodontic braces, or dental veneers. In other implementations, the denture 103 may be a partial denture.

Figure 2:
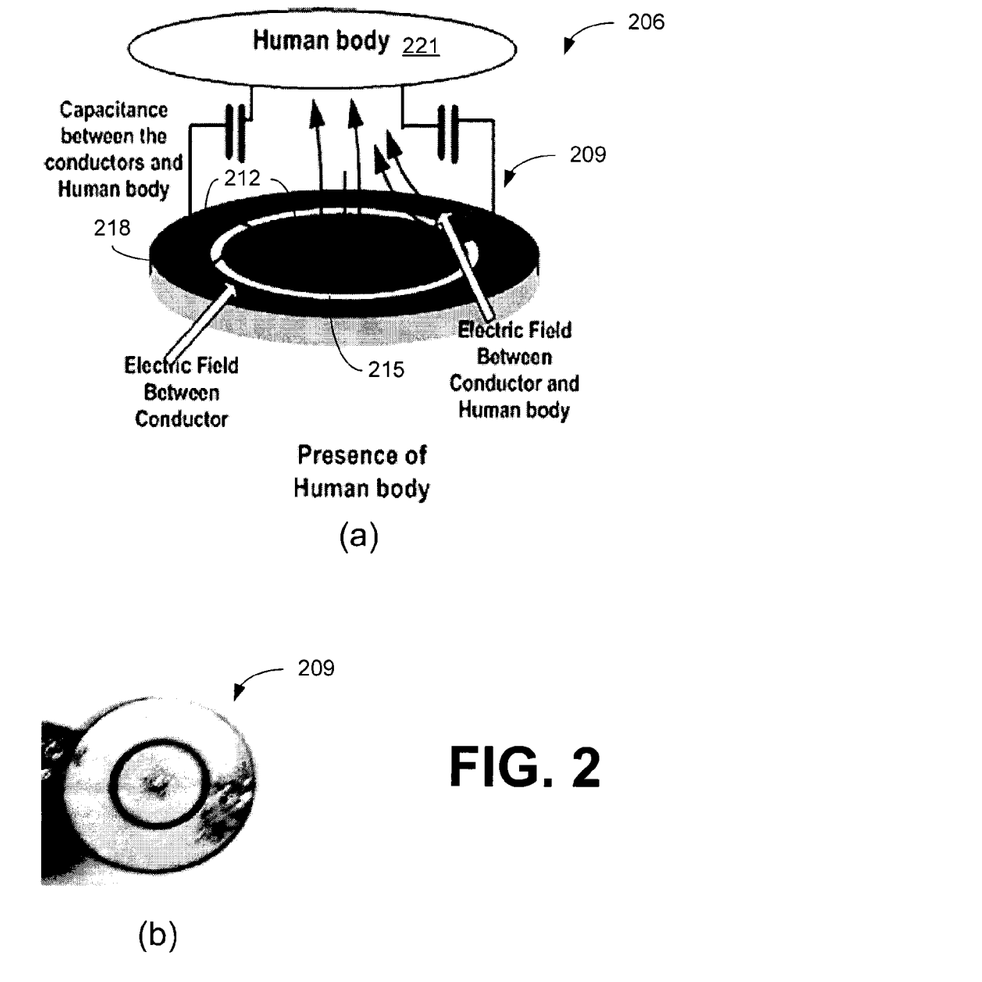
FIGS. 2(a) and 2(b) are an example of a capacitive displacement sensor of the multifunctional denture system of FIG. 1 in accordance with various embodiments of the present disclosure.

A variety of sensors 106 may be used in the multifunctional denture system 100. Referring to FIG. 2(a), shown is a graphical representation of an example of a capacitive displacement sensor 206 that may be included in the denture 103. The capacitive displacement sensor 206 can include a gap capacitor 209 having two co-planar plates 212 separated by a gap 215. In the example of FIG. 2(a), the two co-planar plates 212 are concentric. FIG. 2(b) is a picture of a concentric gap capacitor. When a voltage is applied to the two co-planar plates 212, a fringing electric field 218 is established at the gap 215. When an electric conductor 221 approaches the co-planar conductors 212, the fringing electric field 218 at the gap 215 is disrupted or distorted by the conductor 221. The capacitance of the gap capacitor 209 changes as a function of the distance between the electric conductor 221 and the co-planar plates 212. Since the human body is considered a good conductor 221, the detection of capacitance change can be used as a distance sensing mechanism. The gap capacitor 209 may be embedded in denture 103 to detect the distance between the denture 103 and the oral tissue 221. To increase the sensitivity of the gap capacitor 209, an interdigitated capacitor design or a fractal capacitor design may be used.

Referring next to FIGS. 3(a) and 3(b), shown are examples of strain gauge sensors 306 that may be included in the denture 103. A strain gauge is used to measure the elongation or contraction of an object. When a denture 103 is in contact with the oral tissue 309, a strain gauge sensor 306 can be used for the detection of the dislocation, pressure, and movement of the denture 103 relative to the oral tissue 309. When the Young's modulus of the strain gauge material and the measured strain are known, the stress may be calculated using $\sigma = E \cdot \varepsilon$, where $\sigma$ is the stress, E is the Young's modulus, and $\varepsilon$ is the strain. In general, a mouth can generate a pressure in the range of about 10 lbs. to about 200 lbs. (i.e., 2000 kPa). With this in mind, a strain gauge sensor 306 should withstand this pressure range while being capable of measuring displacement in the range of about 50 µm to about 500 µm.

Figure 3:
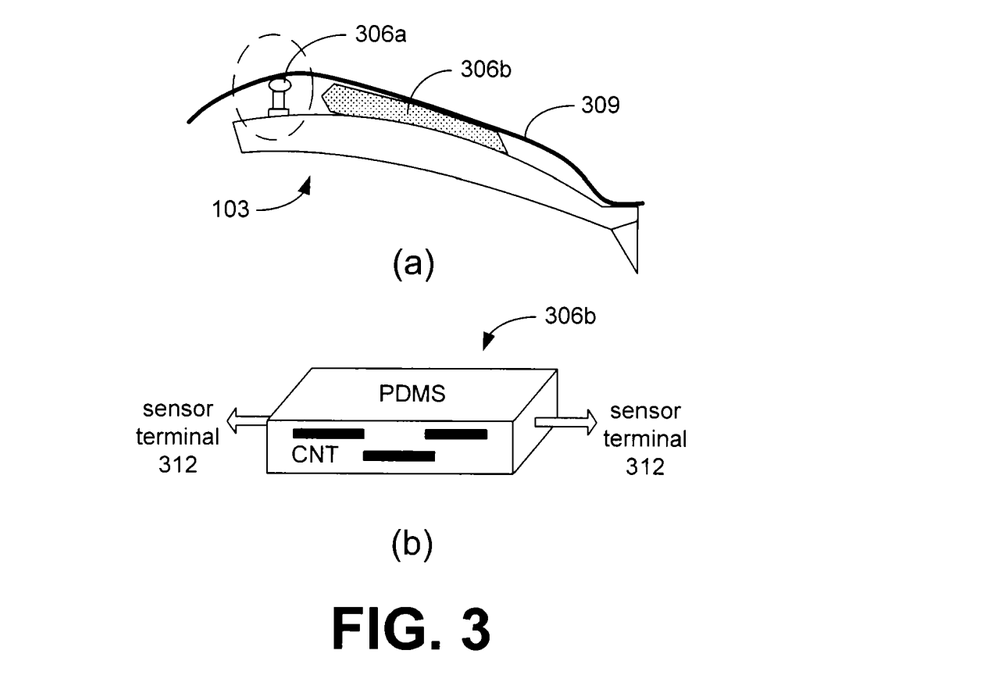
FIGS. 3(a) and 3(b) are examples of strain gauge displacement sensors of the multifunctional denture system of FIG. 1 in accordance with various embodiments of the present disclosure.
Figure 4:
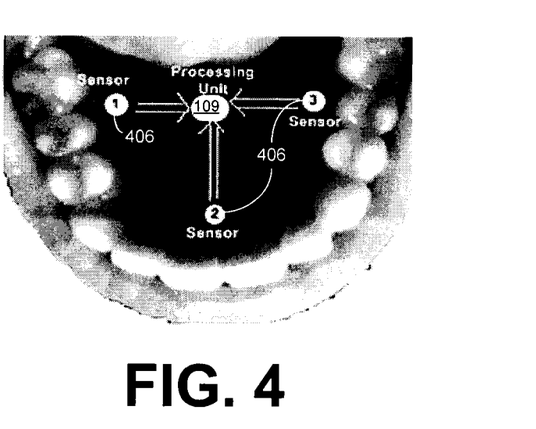
FIG. 4 is an example of the placement of displacement sensors of FIGS. 2 and 3 in the multifunctional denture system of FIG. 1 in accordance with various embodiments of the present disclosure.

FIG. 3 includes examples of two different strain gauge sensors 306a and 306b. The first strain gauge sensor 306a uses a match stick type of strain gauge such as, e.g., a SCP 100 pressure sensor (120 kPa range) from VTI Technologies and a pressure membrane. In the example of FIG. 3(a), the match stick strain gauge 306a contacts the oral tissue 309 along the mouth ceiling. Displacement of the denture 103 distorts the match stick strain gauge generating a signal that can be correlated to the displacement. The second strain gauge sensor 306b utilizes an engineered composite material made of polydimethylsiloxane (PDMS) and carbon nanotubes (CNT) that is positioned between the denture 103 and the tissue 309 of the oral cavity. FIG. 3(b) is a graphical representation of the composite material strain gauge 306b. Distortion of the PDMS/CNT composite material produces a detectable change in the output between sensor terminals 312 that can be correlated to the displacement of the denture 103. To increase the sensing accuracy of denture displacement, data from a plurality of displacement sensors 206/306 located in the denture 103 may be processed. FIG. 4 shows an example of the placement of three displacement sensors 406 (e.g., displacement sensors 206/306) about the denture 103 to obtain accurate displacement indications.

The denture 103 may also include other sensors 106 such as, e.g., temperature sensors and/or chemical and biomedical sensors for monitoring the oral cavity environment. Saliva is a complex oral fluid that serves important functions in maintaining homeostasis of the oral cavity system. Many of the enzymes, hormones, antibodies, antimicrobial constituents, and cytokines in the saliva enter from the blood. This means saliva can provide information not only on the state of oral health, but also on systemic health. For example, biomarkers for oral diseases or other medical diseases such as, e.g., HIV, cancer, and diabetes may be detected in saliva. For instance, glucose sensing may be used for monitoring diabetes.

Figure 5:
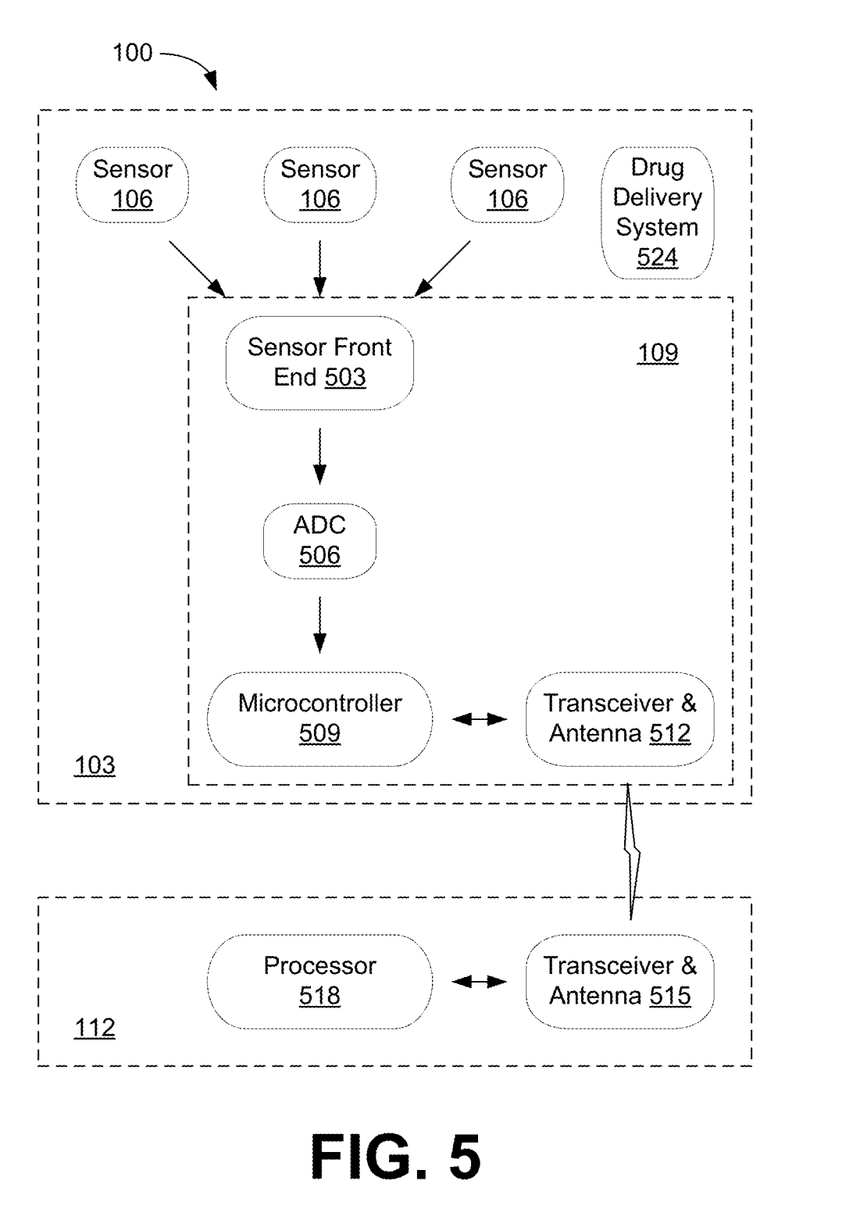
FIG. 5 is a graphical representation of an example of the multifunctional denture system of FIG. 1 in accordance with various embodiments of the present disclosure.

Referring next to FIG. 5, shown is an example of a sensor network of a multifunctional denture system 100. Signals received from one or more sensors 106 mounted in denture 103 may be processed by a sensor front end 503 (e.g., a MUX) and converted by an analog-to-digital converter (ADC) 506 for processing by a microcontroller unit (MCU) 509. The MCU 509 can provide the acquired sensor data from the denture 103 to an external processing unit 112 through a transceiver and antenna 512. In some implementations, the internal module 109 may include memory to store sensor data for subsequent transmission to the external processing unit 112 and/or code or instructions that may be executed by the microcontroller 509. The external processing unit 112 includes a transceiver and antenna 515 that receives the transmitted sensor information and provides it to a processor 518 for analysis and processing. Transmission between the denture 103 and the external processing unit 112 may be over, e.g., a 2.4 GHz communication link.

Figure 10:
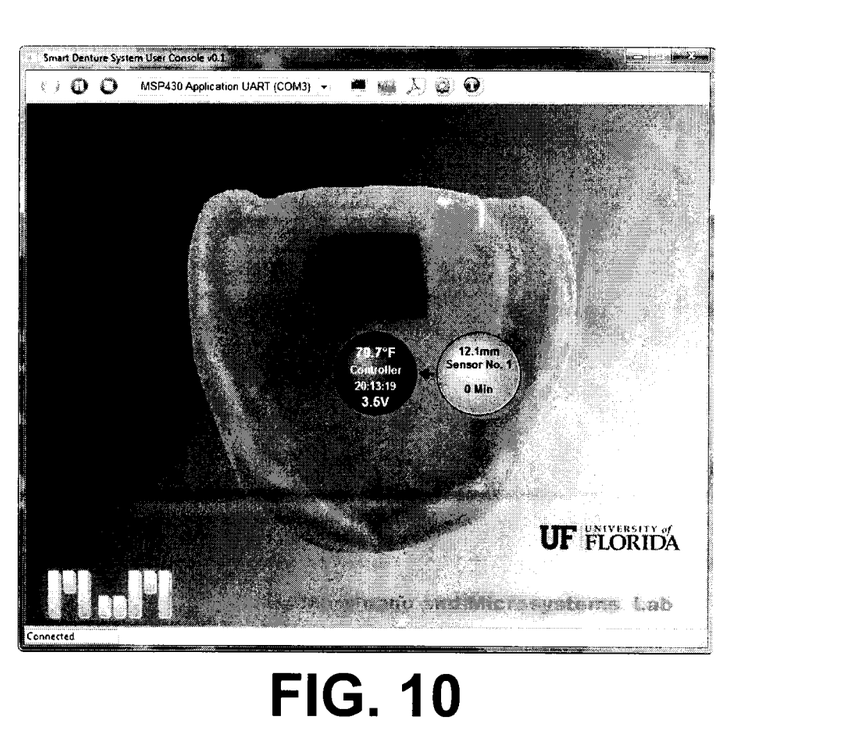
FIGS. 10 and 11 are examples of a graphical user interface shown on a display (e.g., a computer screen) of the multifunctional denture system of FIG. 1 in accordance with various embodiments of the present disclosure.
Figure 11:
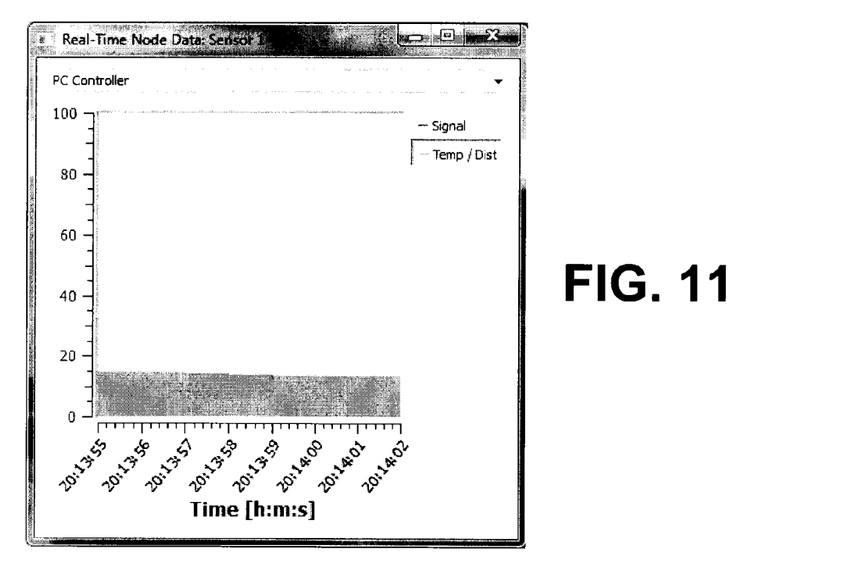

For example, distance information may be obtained by a capacitive sensor 206 (FIG. 2), which is transmitted to an ADC 506 such as, e.g., an AD7746 from Analog Devices. The digitalized signals are fed into a MCU 509 for data processing before being transmitted to a transceiver 512. A CC2510 (Texas Instruments Inc.) may be used as an integrated microcontroller unit and transceiver for more compact and power efficient system implementation. The signal is transmitted over a wireless channel (or link) through a chip antenna 512 and received by a receiver (e.g., CC2500 by Texas Instruments Inc.) and antenna 515. The signal is transferred to a computer or ether processor circuit 518, where it may be rendered and displayed on a screen or display via a graphical user interface (GUI) such as illustrated in FIG. 10. By appropriate processing, the distance information may be extracted from the sensor data and presented on the screen in real time as illustrated in FIG. 11.

Since the sensor network is embedded in the denture 103 where space is limited, the physical and electrical requirements can be stringent. An example of the specifications of the sensor network circuit is listed in TABLE 1. In some embodiments, the sensor network circuit may be implemented using a very large scale integration (VLSI) integrated circuit (IC) approach, which may reduce the size to one tenth the size of the original circuit board. The whole sensor network circuit and micro/nanosensors may be realized in a size scale of a few millimeters or micrometers.

TABLE 1

| Item | Specification |
| --- | --- |
| Board size | 15 mm × 10 mm × 2 mm (L × W × T) |
| Power supply voltage | 3 V ± 0.3 V |
| Current consumption | 17.7 mA (active mode) |
| Precision | 25 μm |
| Measurement range | 15 mm |
| Carrier frequency | ISM 2.4 GHz Band |
| Max. wireless channel distance | 2 meters (may vary) |
| Measurement duration | 20 min. (typical) |
| Weight | 5.19 g (bare board and sensor, battery exclusive) |
| Recharge | "Qi" Compatible wireless recharge |

Figure 6:
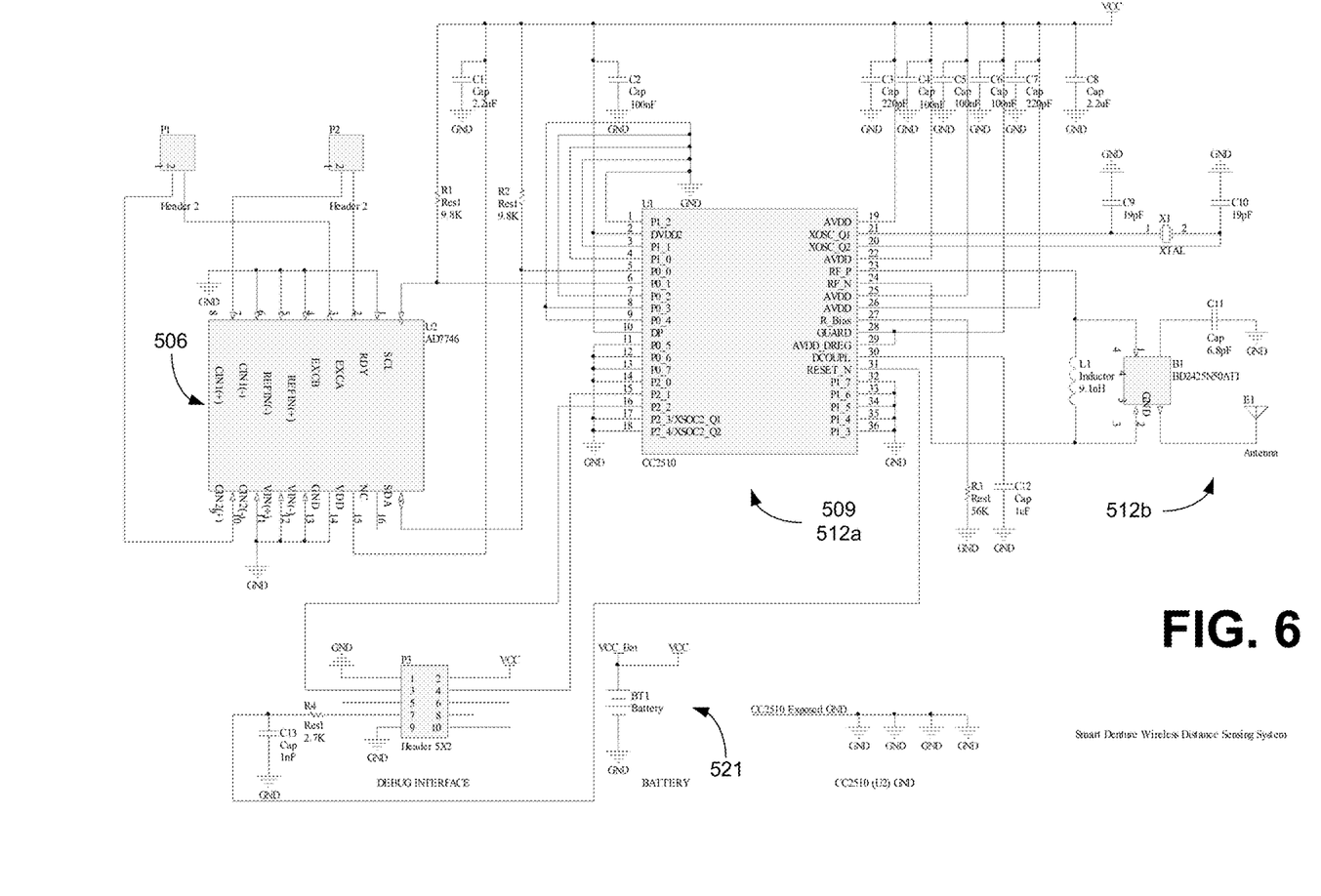
FIG. 6 is a schematic diagram illustrating an example of the multifunctional denture system of FIG. 5 in accordance with various embodiments of the present disclosure.

Referring to FIG. 6, shown is a schematic diagram of an example of an implemented circuit. The example of FIG. 6 includes two main parts: an AD7746 (U2) comprises the sensing front end circuit 506 which receives a capacitance value from, e.g., a capacitive sensor 206 (FIG. 2) and produces an analog voltage output, and subsequently converts it into a digital signal; a CC2510 (U1) comprises the integrated microcontroller 509 and transceiver 512a. AD7746 is a sigma-delta (Σ-Δ) converter which has a capacitance sensing range of about ±4.096 pF with an accuracy of about 4 fF. Also, the example of FIG. 6 includes a built-in temperature sensor with a resolution of 0.1 degree centigrade on board. The digitized capacitance information is transferred to CC2510 (microcontroller 509 and transceiver 512a) for further signal processing and signal modulation for wireless transmission through antenna 512b.

Figure 7:
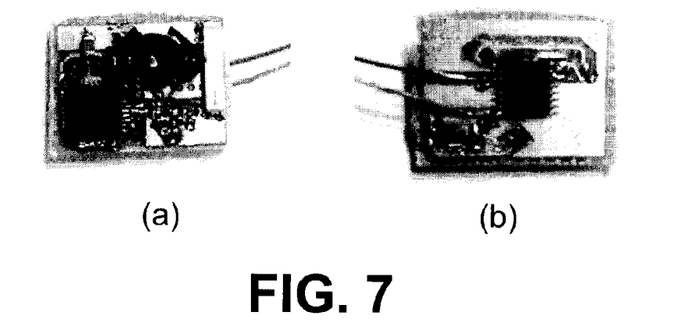
FIGS. 7(a) and 7(b) are an implementation of the multifunctional denture system of FIG. 6 in accordance with various embodiments of the present disclosure.

The CC2510 comprises an enhanced 8051 core MCP 509 as well as an ISM band transceiver 512a. Between the AD7746 sensing front end circuit 506 and the CC2510 microcontroller 509/transceiver 512a, an I2C communication protocol may be used. The digitized distance information is modulated in the CC2510 microcontroller 509 and then transmitted to the free space wireless channel (or link) via a chip antenna 512b. FIG. 7 shows (a) front and (b) back views of a prototype of the circuit of FIG. 6. While the example of FIGS. 7(a) and 7(b) uses off-chip components for the proof of concept, the circuit may be implemented using customized VLSI circuits. The whole electronic circuit and micro/nano sensors may be realized in a size scale of a few millimeters or micrometers.

Figure 8:
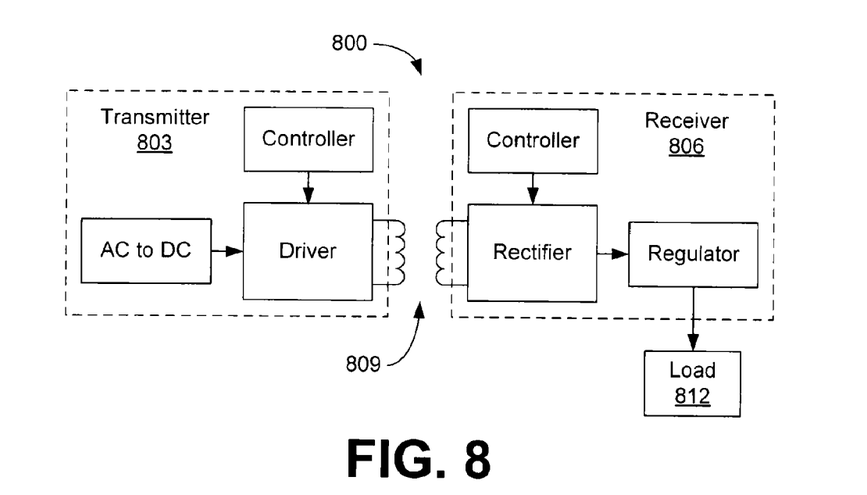
FIG. 8 is a graphical representation of an example of a wireless power delivery system for use in the multifunctional denture system of FIG. 1 in accordance with various embodiments of the present disclosure.

Power for the circuitry may be provided by a power source such as, e.g., a battery 521 (FIG. 6). Considering the sensor network of a multifunctional denture system 100 of FIG. 6 is included in the denture 103, it may be desirable to avoid having to replace the battery 521. A wireless power delivery system may be used to supply power to a rechargeable battery 521 through inductive coupling. Referring to FIG. 8, shown is a graphical representation of a wireless power delivery system 800. Power is delivered between a transmitter 803 and a receiver 806 by inductive coupling between the antennas 809. The delivered power may then be regulated for delivery to a load 812 such as the sensor network. For example, a spiral antenna 809 may be used for near field power coupling and BQ500110 and BQ51013 ICs from Texas Instruments Inc. may be used as the transmitter 803 and the receiver 806, respectively. Since the BQ500110 and BQ51013 ICs are highly integrated chips, nearly no peripherals are required on the receiver side for power collection, making it ideal for device size reduction.

In addition to the sensor network of FIG. 5, the multifunctional denture system 100 may also include drug delivery system 524 that may interface with the internal module 109. The denture 103 may include a sealed reservoir for storing the drug and a dispenser for supplying a defined amount of drug to the oral cavity. In some cases, a plurality of reservoirs may be included with one or more dispensers for delivery of one or more drugs and/or dosages. The internal module 109 may control timing and/or dosage for the delivery system.

Figure 9:
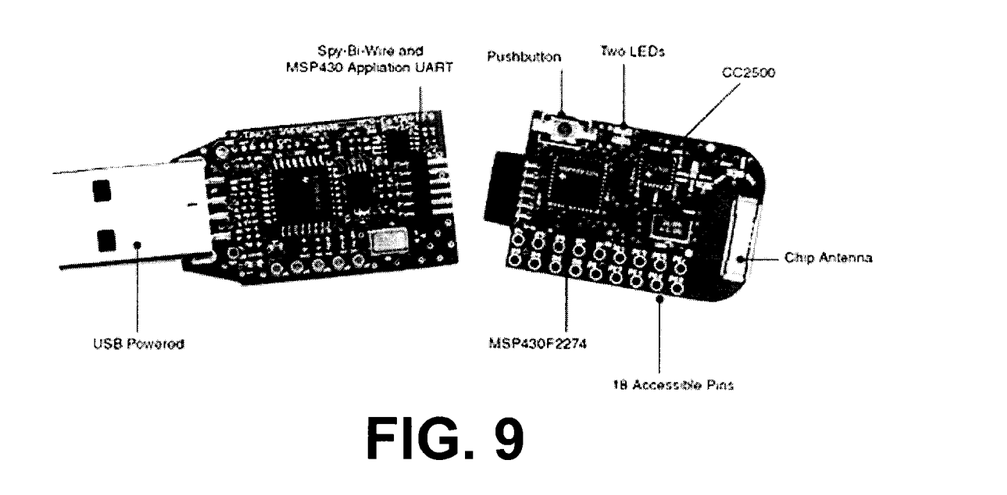
FIG. 9 is an example of a transceiver and antenna used in an external processing unit of the multifunctional denture system of FIG. 1 in accordance with various embodiments of the present disclosure.

Referring back to FIG. 5, the external processing unit 112 includes a transceiver and antenna 515 that receives the transmitted sensor information from the transceiver and antenna 512 and provides it to a processor 518 for analysis and processing. For example, a transceiver and antenna circuit 515 including an MSP430 IC and a CC2500 IC by Texas Instruments Inc. may be provided in, e.g., a USB dongle shape as shown in FIG. 9. The transceiver/antenna circuit 515 may be configured to be plugged into the external processing unit 112 such as, e.g., a computing device (or PC) through a USB connector. Transmission between the denture 103 and the external processing unit 112 may be over, e.g., a 2.4 GHz communication link, a 403-405 MHz medical implant communication service (MICS) band, or other industry science medicine (ISM) bands including, e.g., 433 MHz, 915 MHz, and 5.8 GHz.

Communications between the denture 103 and external processing unit 112 (FIGS. 1 and 5) may be carried out using a variety of communication protocols such as, e.g., SimpliciTI™. SimpliciTI™ is a simple communication protocol especially designed for low cost and small scale network. Since it contains a device switch to change between sleep and active states, it is also known as a low power consuming protocol. Also, certain flexibility is offered and allowing use with multiple network topologies such as peer-to-peer or star network including a central access point, which can be used in the multifunctional denture system 100. The star network configuration allows the external processing unit 112 to communicate with the internal module 109 of one or more denture(s) 103. Two kinds of devices may be used in a star network: a data hub or access point (e.g., a transceiver/antenna circuit 515 of the external processing device) and end devices (e.g., dentures 103). Usually, there is only one access point in a network and it is always on and in charge of network token management (e.g., dentures 103 joining or leaving the network). The access point manages the functionality of end devices such as link listening and receiving. More than one end device can coexist in a network, which are all managed by a single access point.

After an initialization procedure, an end device (e.g., internal module 109 of a denture 103) will transmit a join message to the access point (e.g., transceiver/antenna circuit 515) with a network token in the message. If the join message is identical with that of the access point, an address will be given to the end device by the access point and a communication link is established. To save energy, the end device may enter a sleep state after a data package is transmitted to the access point. For example, after transmitting sensor data to the external processing device 112, the internal module 109 of a denture 103 may sleep for 100 machine cycles before waking up to see if a message or command is waiting on the access point of the external processing unit 112. If there is, the end device (e.g., internal module 109 of denture 103) will turn active and function as desired. Otherwise, the end device enters another sleep period. During the sleep period of the end device, the access point is allowed to process data obtained from the end device and/or communicate with another end device. Since the end device only consumes several micro amperes of currents, this method saves a significant amount of energy in comparison to the case where all end devices are constantly active.

This may be further described in the context of the multifunctional denture system 100 of FIG. 5. Analog sensor data is obtained from one or more sensors 106 and converted by an ADC 506. Where an AD7746 is used as the ADC 506 (FIG. 6), only an I2C communication protocol is supported. The I2C protocol was first introduced by Philips for use in microcontroller data acquisition. To obtain data from, e.g., a capacitive displacement sensor 206 (FIG. 2), three steps can be performed on AD7746: (1) reset the chip then wait for 200 μs; (2) write proper configuration information to corresponding registers such as excitation voltage, measurement frequency, capacitance chop, etc.; and (3) read from corresponding registers where the measured capacitance is stored. The acquired sensor data are then sent to the microcontroller 509 and transceiver 512 (e.g., the CC2510 microcontroller 509/transceiver 512a of FIG. 6) where they are modulated and transmitted to the access point according to the SimpliciTI™ protocol. This may be further connected to a mobile system such as, e.g., a smart phone, a PDA, a tablet (PC) device, a portable computer, or other mobile device to continuously monitor health conditions for patients, realizing "mHealth" (mobile health), a term used for the practice of medicine and public health supported by mobile devices. The mobile device may execute appropriate applications (apps) to implement the mHealth monitoring system.

At the external processing unit 112, a transceiver/antenna 515 such as, e.g., the MSP430-CC2500 based USB dongle of FIG. 9 is programmed based on SimpliciTI requirements and works as the access point of the network. Sensor data are received through the transceiver/antenna 515 and processed by the processor 518 of the external processing unit 112 such as, e.g., a PC for a windows graphical user interface (GUI) to display. An example of a display rendered by a graphics application executed by the processor 519 of the external processing unit 112 is shown in FIG. 10. Temperature, displacement, and other indications may be provided by the GUI including time when the data was obtained.

Real time sensor data may also be rendered for display by the external processing unit 112. Statistic curves may also be rendered for display to provide sensor data such as temperature, displacement, etc. over a period of time. For example, FIG. 11 illustrates a displacement curve, where the x-axis shows time in seconds and the y-axis shows the distance between the denture 103 and the oral tissue 309 (FIG. 3). The curve may be for a single sensor 106 or a combination of sensors 106. The sampling time may be increased or decreased as needed or desired.

Figure 12:
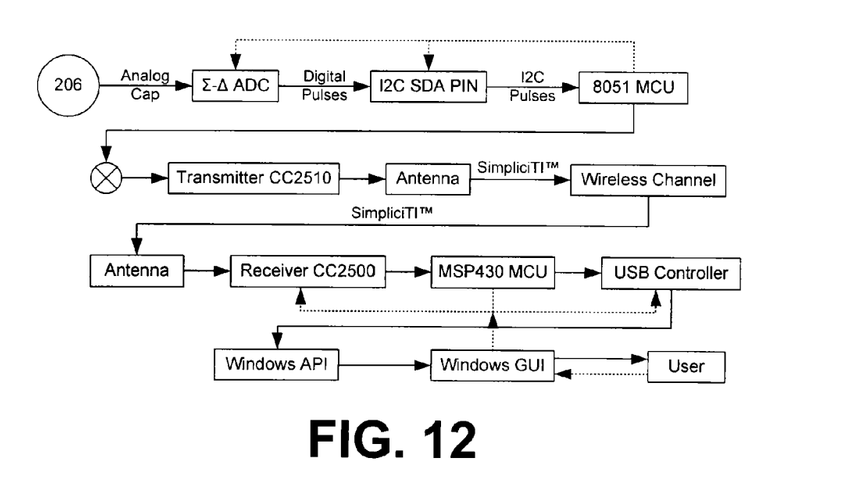
FIG. 12 is an example of the data flow within the multifunctional denture system of FIG. 1 in accordance with various embodiments of the present disclosure.

Referring to FIG. 12, shown is an example of the overall data flow within a multifunctional denture system 100. While the example of FIG. 12 is with respect to a capacitive displacement sensor 206 (FIG. 2), it can be extended to other types of sensors as can be understood. A capacitance signal is first obtained from a capacitive displacement sensor 206 and digitalized by an ADC 506 (e.g., AD7746). The digitalized capacitance information is then sent to microprocessor 509/transceiver 512a (e.g., CC2510) via I2C protocol. The CC2510 chip modulates the capacitance information and transmits the modulated information to the wireless channel via the transmitter antenna 512b. The procedure is guided by the SimpliciTI™ protocol. A transceiver/antenna 515 (e.g., MSP430-CC2500 USB dongle) works as the access point of the external processing unit 112. The transmitted data are received by the receiver antenna of the USB dongle, processed, and sent to the processor 518 of the external processing unit 112 for further processing. The data may then be displayed in a Windows GUI operating within the Windows API. Both real time and statistic data may be made available to the user. The Windows GUI may also allow the user to configure operation of the internal module 109 of the denture 103 through the transceivers and antennas 512 and 515.

For example, to convert the capacitance value to distance, it may be necessary to calibrate the multifunctional denture system 100. For instance, a linear relationship may be assumed between the capacitance and distance (or displacement) values for small distances within, e.g., 15 mm. An accurate distance stage is set to a known distance and the corresponding capacitance measurement is recorded. By measuring multiple data points corresponding to different distances, the relationship between distance and capacitance measurements can be determined as, e.g., a curve and/or an equation. This relationship may then be used to map a measured capacitance value into its corresponding distance (or displacement) information.

When used, the calibration of the multifunctional denture system 100 may be performed as follows: each sensor 106 (FIG. 1) is pre-calibrated in, e.g., a lab and an initial relationship (e.g., an equation) is obtained. Then the denture 103 (FIG. 1) with the embedded sensors 106 is installed in a patient. When the denture 103 is in full contact as determined by a health care professional and/or the patient, sensor measurements or data are obtained and the measurement point is recorded as zero. This zero point information is then used to further correct errors in the initial mapping relationship. Thus, variations from patient to patient may be accounted for. Multiple zero point calibrations might be necessary and multiple measurement results could be averaged to ensure repeatability of the measurements.

Briefly described, one embodiment, among others, comprises a multifunctional oral prosthetic system. The multifunctional oral prosthetic system includes an oral prosthetic device. The oral prosthetic device can include a plurality of sensors and an internal module in communication with the plurality of sensors. The internal module may be configured to provide sensor data corresponding to at least one of the plurality of sensors to an external processing unit when located in an oral cavity. The internal module may be configured to obtain analog signals from each of the plurality of sensors. The plurality of sensors may include a displacement sensor configured to provide an indication of displacement of the oral prosthetic device within the oral cavity, a temperature sensor, a chemical sensor configured to provide an indication of pH level, or a biomedical sensor configured to provide an indication of glucose level. The oral prosthetic device may include a drug delivery system. The drug delivery system may comprise a dispenser configured to supply a defined dosage of a drug to the oral cavity. The internal module may include an analog-to-digital converter (ADC), a microprocessor, and a transceiver embedded in the oral prosthetic device.

The multifunctional oral prosthetic system may comprise the external processing unit configured to obtain the sensor data from the internal module. The external processing unit may be configured to process the obtained sensor data to determine a condition of the oral cavity. The condition of the oral cavity may be a biomarker for an oral disease. The external processing unit may be configured to provide an indication of the condition of the oral cavity through a graphical user interface (GUI). The external processing unit may be configured to process the obtained sensor data to determine a condition of the oral prosthetic device. The condition of the oral prosthetic device may be displacement within the oral cavity. The external processing unit may be configured to provide an indication of the condition of the oral prosthetic device through a graphical user interface (GUI). The denture may comprise a wireless power delivery system. The oral prosthetic device may be a partial denture, a full denture, orthodontic braces, or a dental veneer. The internal module may be configured to communicate with the external processing unit over a wireless channel. The external processing unit may be a cell phone configured to implement a mobile health monitoring system, a PDA configured to implement a mobile health monitoring system, a tablet device configured to implement a mobile health monitoring system, or a portable computer configured to implement a mobile health monitoring system.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A multifunctional oral prosthetic system, comprising:
an oral prosthetic device comprising an upper portion configured to align with a roof of an oral cavity of a wearer, the upper portion of the oral prosthetic device including:
a plurality of sensors embedded in the upper portion including a displacement sensor configured to provide at least one sensor value that corresponds to at least one displacement distance between the upper portion of the oral prosthetic device and the roof of the oral cavity while being worn by the wearer, where the displacement sensor is fixed into a section of the upper portion of the oral prosthetic device that is adjacent to the roof of the oral cavity when worn by the wearer; and
an internal module in communication with the plurality of sensors, the internal module configured to provide sensor data corresponding to at least one of the plurality of sensors to an external processing unit when located in an oral cavity, the sensor data comprising the at least one sensor value, where the external processing unit determines the at least one displacement distance between the upper portion of the oral prosthetic device and the roof of the oral cavity using the at least one sensor value.

2. The multifunctional oral prosthetic system of claim 1, wherein the internal module is further configured to obtain analog signals from each of the plurality of sensors.

3. The multifunctional oral prosthetic system of claim 1, wherein the oral prosthetic device is a denture system that is removable from the oral cavity.

4. The multifunctional oral prosthetic system of claim 1, wherein the plurality of sensors includes a chemical sensor configured to provide an indication of pH level.

5. The multifunctional oral prosthetic system of claim 1, wherein the plurality of sensors includes a biomedical sensor configured to provide an indication of glucose level.

6. The multifunctional oral prosthetic system of claim 1, wherein the oral prosthetic device further comprises a drug delivery system in communication with the internal module, where a drug delivery dosage is controlled by the internal module.

7. The multifunctional oral prosthetic system of claim 6, wherein the drug delivery system comprises a dispenser configured to supply one of a plurality of drugs to the oral cavity.

8. The multifunctional oral prosthetic system of claim 1, wherein the internal module includes an analog-to-digital converter (ADC), a microprocessor, and a transceiver embedded in the upper portion of the oral prosthetic device.

9. The multifunctional oral prosthetic system of claim 1, further comprising the external processing unit configured to obtain the sensor data from the internal module.

10. The multifunctional oral prosthetic system of claim 9, wherein the external processing unit is configured to process the obtained sensor data to determine a condition of the oral cavity.

11. The multifunctional oral prosthetic system of claim 10, wherein the condition of the oral cavity is based at least in part upon evaluation of a biomarker for an oral or other medical disease.

12. The multifunctional oral prosthetic system of claim 10, wherein the external processing unit is further configured to provide an indication of the condition of the oral cavity through a graphical user interface (GUI).

13. The multifunctional oral prosthetic system of claim 9, wherein the external processing unit is configured to process the obtained sensor data to determine a condition of the oral prosthetic device.

14. The multifunctional oral prosthetic system of claim 13, wherein the condition of the oral prosthetic device is indicated by a displacement curve determined using the at least one displacement distance between the upper portion of the oral prosthetic device and the roof of the oral cavity.

15. The multifunctional oral prosthetic system of claim 13, wherein the external processing unit is further configured to provide an indication of the condition of the oral prosthetic device through a graphical user interface (GUI).

16. The multifunctional oral prosthetic system of claim 1, wherein the oral prosthetic device further comprises a wireless power delivery circuit configured to supply power to the oral prosthetic device that was received wirelessly from a transmitting source.

17. The multifunctional oral prosthetic system of claim 1, wherein the oral prosthetic device is a partial denture, a full denture, or orthodontic braces.

18. The multifunctional oral prosthetic system of claim 1, wherein the internal module is configured to communicate with the external processing unit over a wireless channel.

19. The multifunctional oral prosthetic system of claim 18, wherein the external processing unit is a cell phone, a PDA, a tablet, or a portable computer.

20. The multifunctional oral prosthetic system of claim 18, wherein the external processing unit is configured to implement a mobile health monitoring system via an application executed by the external processing unit.

21. A multifunctional oral prosthetic system, comprising:

an oral prosthetic device comprising an upper portion configured to align with a roof of an oral cavity of a wearer, the upper portion of the oral prosthetic device including:

a plurality of sensors embedded in the upper portion including a displacement sensor configured to provide at least one sensor value that corresponds to at least one displacement distance between the upper portion of the oral prosthetic device and the roof of the oral cavity while being worn by the wearer, wherein:

the displacement sensor is fixed into a section of the upper portion of the oral prosthetic device that is adjacent to the roof of the oral cavity when worn by the wearer, and the displacement sensor is a capacitive displacement sensor, where a capacitance of the capacitive displacement sensor varies as a function of the distance between the upper portion of the oral prosthetic device from the roof of the oral cavity; and an internal module in communication with the plurality of sensors, the internal module configured to provide sensor data corresponding to at least one of the plurality of sensors to an external processing unit when located in an oral cavity, the sensor data comprising the at least one sensor value, where the external processing unit determines the at least one displacement distance between the upper portion of the oral prosthetic device and the roof of the oral cavity using the at least one sensor value.

* * * * *